United States Patent [19]

Cheminal et al.

[11] 4,310,697

[45] Jan. 12, 1982

[54] PROCESS FOR THE MANUFACTURE OF DIMETHYLETHYLAMINE

[75] Inventors: Bernard Cheminal, La Chambre; Paul Kiener, Saint Genis Laval; Aime Traversaz, La Chambre, all of France

[73] Assignee: Produits Chimiques Ugine Kuhlmann, Courbevoie, France

[21] Appl. No.: 177,333

[22] Filed: Aug. 12, 1980

[30] Foreign Application Priority Data

Aug. 14, 1979 [FR] France ................................ 79 20650
Jul. 18, 1980 [FR] France ................................ 80 15880

[51] Int. Cl.$^3$ ............................................. C07C 85/06
[52] U.S. Cl. ................................... 564/479; 564/480; 564/497
[58] Field of Search ..................... 564/479, 480, 478

[56] References Cited

U.S. PATENT DOCUMENTS

| | | | |
|---|---|---|---|
| 2,073,671 | 3/1937 | Andrews | 564/479 |
| 2,092,431 | 9/1937 | Swallen et al. | 564/479 |

FOREIGN PATENT DOCUMENTS

| | | | |
|---|---|---|---|
| 2535073 | 2/1977 | Fed. Rep. of Germany | 564/479 |
| 2749066 | 5/1978 | Fed. Rep. of Germany | 564/479 |
| 2709864 | 8/1978 | Fed. Rep. of Germany | 564/479 |
| 2844984 | 4/1979 | Fed. Rep. of Germany | 564/479 |

OTHER PUBLICATIONS

Morrison and Boyd, "Organic Chemistry," 3rd Ed., p. 630, (1973).
Rose, "The Condensed Chemical Dictionary," 5th Ed., p. 568 (1956).
Baiker et al., "Tetrahedron Letters," (22), pp. 1937–1938 (1977).

*Primary Examiner*—John Doll
*Attorney, Agent, or Firm*—Sigalos & Levine

[57] ABSTRACT

This invention relates to a process for the manufacture of dimethylethylamine comprising reacting gaseous ethanol with a gaseous mixture of hydrogen and dimethylamine in the presence of a hydrogenation/dehydrogenation catalyst comprising copper and chromic oxide alone or admixed with barium oxide, zinc oxide, magnesium oxide, or other oxides, at a temperature of about 180° C. to 240° C. and an absolute pressure of about 1 to 15 bars for a time sufficient to form dimethylethylamine, the molar ratio of dimethylamine/ethanol being about 0.2 to 0.6 and the molar ratio of hydrogen/ethanol being about 3 to 10.

11 Claims, 1 Drawing Figure

PROCESS FOR THE MANUFACTURE OF DIMETHYLETHYLAMINE

BACKGROUND OF THE INVENTION

The present invention concerns a process for the preparation of dimethylethylamine:

by the reaction of ethanol with dimethylamine according to the reaction:

This reaction is carried out in the presence of hydrogen and of a hydrogenation/dehydrogenation catalyst.

Dimethylethylamine is an industrial product used as a polymerization catalyst for polyurethane resins principally used in the manufacture of foundry casting molds by the so-called 'cold box' process.

The catalytic amination of alcohols in the presence of hydrogenation/dehydrogenation catalysts and, if need be, of hydrogen is already known in particular by Houben-Weyl, Vol. 11/1, pages 126 and following.

In a more precise manner, A. Baiker and W. Richarz (Industrial and Engineering Chemistry, Product Research and Development, 1977, 16 (3), pages 261 to 266) describe the catalytic amination of long chain aliphatic alcohols in the presence of various catalysts, among them copper and chromic oxide based catalysts.

However, during the dimethylamination of n-dodecanol, for instance, which is cited in Table III of page 265 of that article, these authors employ a molar ratio of (dimethylamine/dodecanol)=5.5, which during an industrial exploitation of this process results in a very large amount of recycling of the excess dimethylamine, bringing about a loss of productivity and a consumption of energy accrued in the form of vapor. The behavior of the catalyst with time, moreover, is not mentioned.

French patent No. 2,320,287 describes the reaction in the liquid phase, of long chain alcohols with primary or secondary N-methylated amines in the presence of copper chromite. However, the reaction times are long (5 to 7 hours in the examples of discontinuous operations), and the alkylamination is carried out in a complex equipment set-up, resulting in a low productivity and expensive upkeep. The use of catalysts in very finely powdered form implies extremely long filtration times, above all in the presence of viscous products like long chain N-methylated amines. Examples 1 to 8, giving a bracket for the concentration of dimethylamine in the circulation gas consisting of hydrogen for the essential part, do not permit a precise calculation of the molar ratio of (dimethylamine/alcohol) (thus the true consumption of dimethylamine), although it is possible to estimate that the latter is located in the vicinity of 1, that is to say in the vicinity of the theoretical molar ratio. Furthermore, no indication is given on the useful life of the catalysts being employed. Finally, the reaction temperature is such that this technique does not adapt itself to alcohols having a low boiling point, such as ethanol, on one hand because its use would require a high operating pressure in order to operate in the liquid phase and on the other hand because the first members of the series of aliphatic alcohols dehydrogenate at a much higher temperature than do the alcohols possessing longer chains.

SUMMARY OF THE INVENTION

The present invention provides a process for the economical preparation of dimethylethylamine by the dimethylamination of ethanol in the gaseous phase, a process which furnishes high yields of that amine with practically complete conversion.

Briefly stated, the present invention comprises a process for the manufacture of dimethylethylamine comprising reacting gaseous ethanol with a gaseous mixture of hydrogen and dimethylamine in the presence of a hydrogenation/dehydrogenation catalyst at a temperature of about 180° to 240° C. and an absolute pressure of about 1 to 15 bars for a time sufficient to form the dimethylethylamine; the molar ratio of dimethylamine/ethanol being about 0.2 to 0.6 and the molar ratio of hydrogen/ethanol being about 3 to 10.

DETAILED DESCRIPTION

With the present invention, it is possible to obtain the dimethylethylamine with a quantitative degree of conversion of the dimethylamine and of the theoretically convertible ethanol, with a yield of 97% in relation to the dimethylamine and a yield of 97% in relation to the converted ethanol, while the secondary products present in the reaction mixture do not interfere with the later isolation of a dimethylethylamine having a high degree of purity. Moreover, the quantity of these secondary products obtained by the dehydrogenation of the excess ethanol and the autocondensation of the acetaldehyde having thus been generated, or by the reaction of this same acetaldehyde with the dismutation compounds of the dimethylamine, is low, and their percentage by weight in relation to the dimethylethylamine produced can be kept at a value below 3%. The acetaldehyde can, moreover, subsequently either be destroyed by hydrazine hydrate or catalytically rehydrogenated into ethanol at a lower temperature (100° to 130° C.) under the same absolute pressure (8 bars) or a pressure close to this value. The aminated secondary products can easily be separated from the dimethylethylamine by distillation.

The process of the invention can be implemented in the manner described below. The dimethylamine (stored in the liquid state in a reservoir kept under nitrogen pressure) and the liquid ethanol are introduced in continuous manner into an evaporator consisting, for instance, of a jacketed, steam-heated tube, and are mixed with the hydrogen in the desired proportions and this is done in the most homogeneous manner possible. The molar ratio of (hydrogen/ethanol) is between 3 and 10, preferably close to 5. The gaseous mixture then traverses the reactor consisting of a tube heated by a bath of molten salts kept at a temperature between 180° and 240° C., and preferably close to 200° C., containing the catalyst. The contact time of the gases in the reactor can be estimated at a few seconds; 2 to 10 seconds, depending on the operating conditions. The absolute pressure inside of the reactor and of its attachments is.

kept between 1 and 15 bars and, preferably, close to 8 bars.

The gaseous reaction effluent traverses a series of water-cooled condensers and then a separator, in which the obtained liquid is withdrawn in continuous manner and in which the uncondensed gases (essentially consisting of hydrogen and of 1 to 2% of dimethylethylamine by volume) are recycled to the evaporator with the help of a circulation pump, after having traversed an absorption column capable of functioning either as a washer (by spraying the gas loaded with amine with water or ethanol) or to rid this gas of all liquid particles. Considering that during the course of the process slight quantities of gaseous secondary products, principally consisting of hydrocarbons, are formed, it is necessary to partially replace the recycling gas by fresh hydrogen (about 0.1 to 1% and, preferably, 0.2 to 0.7% by volume).

Contrary to the indications given in French Pat. No. 2,320,287 which has already been cited and which claims a molar ratio of (dimethylamine/alcohol) close to 1 or a little above, the upper limit of this ratio for the present invention is located at about 0.6. The molar ratio can be between 0.2 to 0.6; preferably between 0.25 to 0.40. Above 0.6, very large quantities of aminated secondary products (trimethylamine, methyldiethylamine, methylethylamine, dimethylbutylamine) are formed, resulting in an intolerable drop in the values of the yields and considerably interfering with the later isolation of the dimethylethylamine. The use of such a molar ratio, however, results in a slight formation of acetaldehyde which, unlike the aminated secondary products, can be reconverted into ethanol by a post-catalytic hydrogenation at low temperature (100° to 130° C.). Another means making it possible to eliminate the very slight quantities of this by-product consists in treating the reaction mixture with hydrazine hydrate by adding at the most, 3 times the stoichiometric quantity necessary to convert the acetaldehyde.

The present invention most particularly concerns the dimethylamination of ethanol, but it can be applied to other primary or secondary amines like methylamine, ethylamine, propylamine, isopropylamine, and to other primary alcohols like propanol and butanol or secondary alcohols (isopropyl alcohol, secondary butanol).

The catalysts used are catalysts composed of copper, copper oxide (cupric oxide) and chromic oxide, either mixed or not mixed with barium oxide, zinc oxide, magnesium oxide and other oxides, and supported in such a way that the content of active substance is between 85 and 95%, that is to say with 5 to 15% as catalyst support. Particularly suitable is a catalyst whose composition by weight, after reduction, is the following:

| | |
|---|---|
| Copper | 31% |
| Chromium | 25% |
| Barium | 10% |

That is to say with an atomic ratio of $\underline{Cu} = 1.02$ and an atomic ratio of $\underline{Ba} = 0.15$.
$\phantom{That is to say with an atomic ratio of }Cr$
$\phantom{atomic ratio of }Cu$ The catalysts are preferably supported with an inert support like silica and put in the form of beads, extrudates, small balls or compressed tablets, but preferably in the form of cylindrical pellets having a diameter and a thickness of 3 to 6 mm. The expectation for the useful life of a catalytic charge can be estimated at about 2000 hours (3 months).

The catalyst can be regenerated by an oxidation of the carbonaceous matter by a mixture of air diluted in nitrogen, followed by a reduction by a mixture of hydrogen and steam. The regenerated catalyst presents a very slight drop in activity compared to its activity in the original state when new, but this method makes it possible to carry out manufacturing runs of the order of several months.

When the post-catalysis is implemented, it is possible to use catalysts identical to those of the main reaction or different hydrogenation catalysts.

The invention will be further described in connection with the following examples which are set forth for purposes of illustration only.

EXAMPLE 1

Figure 1:
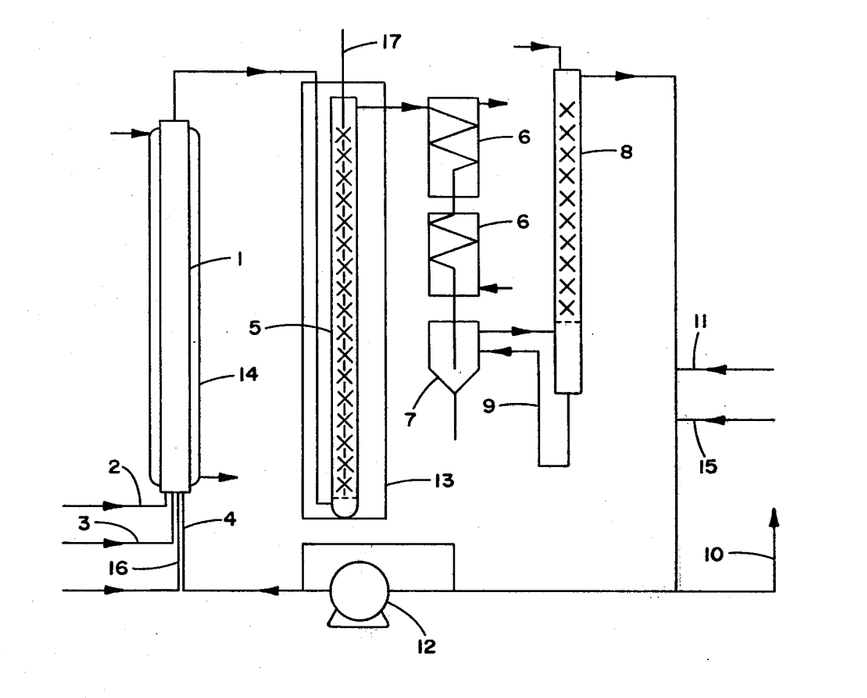
The single FIGURE is a schematic drawing of an apparatus system suitable for carrying out the present invention.

The reaction is carried out in the equipment set-up illustrated in the FIGURE. The apparatus consists of an evaporator (1) into which the liquid anhydrous dimethylamine is introduced by duct (2), the liquid azeotropic ethanol is introduced by duct (3), and the recycling gas is introduced by duct (4), a monotubular reactor (5) of 2-liter capacity, two cold water-cooled condensers in series (6), a separator (7), a washer (8) whose liquid phase is joined up with the separator via duct (9), a duct (10) for the evacuation of the gases, a duct (11) for supplying fresh hydrogen under pressure, a gas recycling pump (12), and a duct (15) for supplying nitrogen. Heating of the reactor is ensured by a molten salts bath contained in tank (13). A duct (16) makes it possible to bring in water for the reduction of the catalyst. The evaporator is steam-heated with the help of the jacket (14). The reactor is equipped with a thermometer well (17) which makes it possible to measure the temperature profile all along the reaction tube and inside of the catalytic bed by means of a thermocouple. This equipment serves, on one hand, to follow the temperature of the catalyst and, on the other hand, to examine the evolution of the degree of advancement of the reaction all along the monotubular reactor during the course of operation.

2,800 g of copper chromite catalyst (31% Cu, 25% Cr, 10% Ba) in the form of pellets of 4.5×4.5 mm are placed into the reactor (5) having a capacity of 2 liters; the apparatus is flushed with nitrogen via duct (15) and then with hydrogen and steam in a molar ratio of the order of 20 to 25 via ducts (11) and (16) in such a way that the peak temperature inside of the catalytic bed does not exceed 250° to 260° C. for a temperature of 230° C. for the salts bath contained in tank (13). When the peak temperature arrives at the top of the bed of the catalyst, the reduction of the latter is terminated and the temperature of the bath is brought to about 200° C. The absolute pressure of the installation is brought to 4 bars by means of hydrogen via duct (11) and by pump (12) having been started up in such a way as to implement a gas circulation at a flow rate of 2,780 Nl/h (124 moles $H_2$/h) in the installation, with this pressure being kept constant. Anhydrous (water-free) liquid dimethylamine is then injected via duct (2) at a flow rate of 424 g/h (9.4 moles/h) and the azeotropic ethanol is injected via duct (3) at a flow rate (calculated in pure ethanol) of 1,428 g/h (31 moles/h). This trial is thus carried out with the following molar ratios:

(Dimethylamine/ethanol) = 0.30

(hydrogen/ethanol)=4

A purge of the recycling gas via duct (10) at a flow rate of 18 Nl/h makes it possible to regularly evacuate the gaseous by-products and to maintain a constant pressure in the apparatus by replacing the gases having been eliminated with fresh hydrogen by means of duct (11). The temperature profile measured with the help of the sliding thermocouple in well (17) indicates a maximum temperature of 205.5° C. to appear at 50 cm from the bottom of the catalytic bed (whose total height is 3 m). The liquid reaction effluent is continuously withdrawn via duct (18) during 1 hour. There is thus obtained a crude mixture containing 670 g of dimethylethylamine and 990 g of unconverted ethanol. In relation to the quantity theoretically capable of being converted into dimethylethylamine, the alcohol has reacted with a degree of conversion of 102.3%. The dimethylamine has been completely converted and the yield based on dimethylamine is 97.3%, while the yield in relation to the converted ethanol is 96.2%. The percentages of by-products by weight, expressed in relation to the dimethylethylamine having been formed, are the following:

| | |
|---|---|
| trimethylamine | 1% |
| methyldiethylamine | 1.4% |
| dimethylbutylamine | 0.6%. |

The acetaldehyde having been generated corresponds to 0.4% of the dimethylethylamine produced. This content, which is troublesome for the separation by distillation of the pure dimethylethylamine, can be diminished in notable manner by treating the gaseous effluent from reactor (5) at about 100° C., on the same catalyst and under an absolute pressure of 4 bars. It is likewise possible to get rid of this impurity by an appropriate treatment with hydrazine hydrate.

EXAMPLE 2

This reaction is carried out in the same equipment set-up and with the same catalyst as those specified in Example 1, under the following operating conditions:
(a) temperature of the bath=210.5° C.,
(b) flow rate of the dimethylamine=466 g/h (10.33 moles/h);
(c) flow rate of the pure ethanol=1,380 g/h (29.95 moles/h); and
(d) flow rate of the hydrogen=3,360 Nl/h (150 moles/h).

That is to say with the following molar ratios:

(dimethylamine/ethanol)=0.35

(hydrogen/ethanol)=5

By operating as in Example 1, the following results are obtained:
(i) degree of conversion of the theoretically convertible ethanol=101%;
(ii) degree of conversion of the dimethylamine=100%;
(iii) yield of dimethylethylamine in relation to the dimethylamine involved=97.0%;
(v) yield of dimethylethylamine in relation to the converted ethanol=93.3%; and
(v) percentages of the principal by-products by weight, in relation to the dimethylethylamine formed in the crude reaction effluent:

| | |
|---|---|
| trimethylamine | 1.1% |
| methyldiethylamine | 1.6% |
| dimethylbutylamine | 0.6% |

These results were obtained after 185 hours of continuous operation on the same charge of catalyst.

EXAMPLE 3

9,800 g of the catalyst described in Example 1, in the form of pellets having dimensions of 4.5×4.5 mm are placed into a monotubular reactor analogous to the one described in Example 1, but having a capacity of 7 liters. The trial is carried out under the following operating conditions:
(a) temperature of the salts bath=200° C.;
(b) absolute pressure=4 bars;
(c) flow rate of the ethanol (in pure ethanol)=4,631 g/h (100.52 moles/h);
(d) flow rate of the dimethylamine=1,519 g/h (33.68 moles/h); and
(e) flow rate of the hydrogen=11,200 Nl/h (500.0 moles/h)

which corresponds to the following ratios:

molar ratio of (dimethylamine/ethanol)=0.34 molar ratio of (hydrogen/ethanol)=5

The following results are obtained:
(i) degree of conversion of the theoretically convertible ethanol=102.7%;
(ii) yield of dimethylethylamine in relation to the converted ethanol=95.2%;
(iii) degree of conversion of the dimethylamine=100%; and
(iv) yield of dimethylethylamine in relation to the dimethylamine involved=96.9%.

The percentages of the principal by-products by weight, in relation to the dimethylethylamine manufactured, are the following:

| | |
|---|---|
| trimethylamine | 0.8% |
| methyldiethylamine | 1.1% |
| acetaldehyde | 0.7% |

EXAMPLE 4

This example illustrates the obtaining of an effluent which is practically devoid of acetaldehyde due to post-catalytic treatment of the effluent issuing from the reactor (5).

The principal reaction carried out on the same charge of catalyst as the one described in Example 2 and under the same conditions, but with a molar ratio of (dimethylamine/ethanol)=0.33, gives the following results obtained after analysis of an instantaneous sample:

percentages of by-products by weight, in relation to the obtained dimethylethylamine:

| | |
|---|---|
| trimethylamine | 1% |
| methyldiethylamine | 1.5% |
| dimethylbutylamine | 0.2% |
| acetaldehyde | 2.2% |

The liquid reaction effluent obtained in the reactor (5) at the end of the trial described above is retreated in an apparatus analogous to the one of Example 1, but not including any gas recycling and the monotubular reactor, which is heated by an electric resistance and not by a bath of molten salts, has a capacity of 0.5 liters. The evaporator is likewise heated by means of an electric resistance. 700 g of the same copper chromite catalyst as the one described in Example 1 are placed into this reactor, and it is reduced in analogous manner, but by replacing the steam by nitrogen. The above liquid effluent at a flow rate of 660 g/h is supplied with a flow rate of hydrogen of 750 Nl/h (33.5 moles of $H_2$/h). The reactor is kept under an absolute pressure of 4 bars and at a temperature of 100° C. The crude product having been treated thus, is collected in the liquid state and an analysis of an instantaneous sample is made.

The acetaldehyde content in relation to the dimethylethylamine is below 0.1% by weight and the slight yellow coloration of the effluent from reactor (5), obtained in the first phase of the operation, has disappeared, with the product obtained after this post-catalysis treatment being perfectly colorless.

The yield of dimethylethylamine in relation to the converted ethanol goes from 93.7% in the principal step to 96.4% after post-catalysis, proving that the residual acetaldehyde was easily rehydrogenated into ethanol during the second step.

EXAMPLES 5 to 12

In order to show the influence exerted by the molar ratio of (dimethylamine/ethanol) on the yield of desired product, and thus on the economy of the process, the following trials are carried out:

The two trials of a first series were carried out on a copper chromite catalyst whose atomic composition is the following:

atomic ratio of (Cu/Cr)=0.8 atomic ratio of (Ba/Cu)=0.101 utilized in the form of pellets having dimensions of 3.2×3.2 mm.

At a temperature of 180° C., with a flow rate of pure ethanol of 111 g/h (2.4 moles/h) and a molar ratio of (hydrogen/ethanol)=3, the following results are obtained:

TABLE I

| Example | Molar Ratio of DMA* ethanol | Degree of conversion of the ethanol | Yield of DMEA** in relation to the ethanol | Degree of conversion of the (theoretically convertible) DMA* | Yield of DMEA** in relation to the DMA* % | Yield of by-product in relation to the dimethylamine % | | |
|---|---|---|---|---|---|---|---|---|
| | | | | | | trimethyl-amine | methyl-ethylamine | methyl-diethyl-amine |
| 5 | 3.0 | 52.6 | 95.0 | 59.0 | 74.0 | 9.0 | 3.6 | 0.8 |
| 6 | 1.5 | 63.7 | 89.2 | 71.8 | 76.6 | 8.0 | 2.7 | 2.1 |

*Dimethylamine
**Dimethylethylamine

The two trials of the following series were carried out on a copper chromite catalyst whose atomic composition is the following:
atomic ratio of (Cu/Cr)=0.9
atomic ratio of (Ba/Cu)=0.01
utilized in the form of pellets having dimensions of 5 mm×5 mm.

At a temperature of 200° C., with a flow rate of pure ethanol of 228 g/h (5.0 moles/h) and a molar ratio of (hydrogen/ethanol)=3, the following results are obtained:

TABLE II

| Example | Molar Ratio of DMA* ethanol | Degree of conversion of the ethanol | Yield of DMEA** in relation to the ethanol | Degree of conversion of the (theoretically convertible) DMA* | Yield of DMEA** in relation to the DMA* % | Yield of by-product in relation to the dimethylamine % | | |
|---|---|---|---|---|---|---|---|---|
| | | | | | | trimethyl-amine | methyl-ethylamine | methyl-diethyl-amine |
| 7 | 1.5 | 59.5 | 79.6 | 46.8 | 75.0 | 7.8 | 3.7 | 2.1 |
| 8 | 1.1 | 60.3 | 74.9 | 61.5 | 73.4 | 6.2 | 2.7 | 3.5 |

Dimethylamine
**Dimethylethylamine 0.5 liters of the copper chromite catalyst in pellet form are placed into the reactor described in the second phase of Example 4, this catalyst is reduced in the usual manner and various mixtures of hydrogen, ethanol and dimethylamine in gas form under an absolute pressure of 4 bars are passed over it. Four series of trials are thus carried out on analogous copper chromite catalysts.

The two trials of the following series were carried out on the same catalyst as the one described in Examples 7 and 8.

At a temperature of 215° C., with a flow rate of pure ethanol of 226 g/h (4.9 moles/h) and a molar ratio of (hydrogen/ethanol)=7.3, the following results are obtained:

TABLE III

| Example | Molar Ratio of DMA* ethanol | Degree of conversion of the ethanol | Yield of DMEA** in relation to the ethanol*** | Degree of conversion of the DMA* | Yield of DMEA** in relation to the DMA* % | Yield of by-product in relation to the dimethylamine % | | |
|---|---|---|---|---|---|---|---|---|
| | | | | | | trimethyl-amine | methyl-ethylamine | methyl-diethyl-amine |
| 9 | 0.5 | 103.9 | 85.4 | 99.2 | 88.9 | 1.5 | 0.1 | 4.8 |
| 10 | 0.3 | 96.9 | 87.4 | 100.0 | 85.3 | 0.9 | 0 | 4.1 |

*Dimethylamine
**Dimethylethylamine
***Theoretically convertible

The two trials of this (the following) series were carried out on a copper chromite catalyst whose atomic composition is the following:
  atomic ratio of (Cu/Cr)=1.5
  atomic ratio of (Ba/Cu)=0

At a temperature of 180° C., with a flow rate of pure ethanol of 341 g/h (7.4 moles/h) and a molar ratio of (hydrogen/ethanol)=6.5, the following results are obtained:

TABLE IV

| Example | Molar Ratio of DMA* ethanol | Degree of conversion of the ethanol | Yield of DMEA** in relation to the ethanol*** | Degree of conversion of the DMA* | Yield of DMEA* in relation to the DMA* % | Yield of by-product in relation to the dimethylamine % | | |
|---|---|---|---|---|---|---|---|---|
| | | | | | | trimethyl-amine | methyl-ethylamine | methyl-diethyl-amine |
| 11 | 0.5 | 91.0 | 87.6 | 88.7 | 89.8 | 2.5 | 0.8 | 4.2 |
| 12 | 0.3 | 103.5 | 87.6 | 100.0 | 94.4 | 1.2 | 0 | 2.3 |

*Dimethylamine
**Dimethylethylamine
***Theoretically convertible

It can be seen according to Tables I to IV that whatever the atomic composition of the employed copper chromite catalyst, the temperature, the flow rate of the ethanol, and the molar ratio of (hydrogen/ethanol) may be, the influence of the molar ratio of (dimethylamine/ethanol) predominates. This fact is particularly clear in Examples 11 and 12, in which it can be seen that the optimum value of the molar ratio of (dimethylamine/ethanol) is located at about 0.30. It must be added that the presence of methylethylamine in the crude effluent directly interferes with the quality of commercially pure dimethylethylamine, since this impurity, whose boiling point is very close to that of the dimethylethylamine, cannot be separated from the latter by distillation. The fact of working with a molar excess of ethanol in relation to the dimethylamine results in the formation of acetaldehyde, in regard to which as is seen in Example 4 it can be entirely rehydrogenated into ethanol. Thus recovered, among other consequences, it results in an increase of the yield of dimethylethylamine in relation to the ethanol.

EXAMPLE 13

This example illustrates the effect of the pressure on the results.

The same trial as the one described in Example 2 is carried out, but with the following operating conditions:
  (a) bath temperature=202° C.,
  (b) absolute pressure=8 bars,
  (c) flow rate of dimethylamine=637 g/h (14.12 moles/h),
  (d) flow rate of pure ethanol=2,123 g/h (46.09 moles/h), and
  (e) flow rate of hydrogen=5,150 Nl/h (230 moles/h).
That is to say, with the following molar ratios:
  (dimethylamine/ethanol)=0.31
  (hydrogen/ethanol)=5
The following are the results obtained:
  (i) degree of conversion of the theoretically convertible ethanol=101.8%,
  (ii) yield of dimethylethylamine in relation to the converted ethanol=97.8%,
  (iii) degree of conversion of the dimethylamine=100.0%, and
  (iv) yield of dimethylethylamine in relation to the dimethylamine involved=98.0%.

The weight percentages (of by-products) in relation to the manufactured dimethylethylamine are the following:

| | |
|---|---|
| trimethylamine | 0.9% |
| methyldiethylamine | 0.9% |
| triethylamine | 0.07% |
| acetaldehyde | 0.4% |
| methanol | 0.1% |

The corresponding productivity is increased by about 50% as compared to an operation under an absolute pressure of 4 bars under the same operating conditions.

EXAMPLE 14

11,060 g of a copper chromite catalyst (43% CuO, 43% $Cr_2O_3$, 8% BaO) in the form of pellets having dimensions of 4.8×4.8 mm are placed into a monotubular reactor analogous to the one described in Example 1, but having a capacity of 7 liters. After having accomplished the reduction of the catalyst as described in Example 1, the trial is carried out under the following conditions:
  (a) bath temperature=210° C.,
  (b) absolute pressure=8 bars,
  (c) flow rate of dimethylamine=2,132 g/h (47.28 moles/h),
  (d) flow rate of ethanol (in pure product)=7,284 g/h (158.12 moles/h),
  (e) flow rate of hydrogen=15,859 Nl/h (708 moles/h).
That is to say, with the following molar ratios:

(dimethylamine/ethanol)=0.30 hydrogen/ethanol)=4.5

The results obtained are the following:
  (i) degree of conversion of the theoretically convertible ethanol=99.4%,
  (ii) degree of conversion of the dimethylamine=100%,
  (iii) yield of dimethylethylamine in relation to the dimethylamine involved=97.0%, and
  (iv) yield of dimethylethylamine in relation to the converted ethanol=97.0%.

EXAMPLE 15

This example illustrates the obtaining of a colorless effluent free of acetaldehyde by post-catalytic treatment of the liquid effluent, freed of noncondensable substances, issued from the catalysis reactor and containing variable proportions of acetaldehyde.

This treatment is carried out by the hydrogenation of the acetaldehyde in the liquid phase according to a technique in which the liquid to be treated and the hydrogen under pressure run through a bed of hydrogenation catalyst from top to bottom, in co-current flow.

The effectiveness of the treatment is followed by means of a qualitative test called the 'silver mirror test' which makes it possible to detect traces of aldehydes.

By means of a pump, the liquid effluent from the catalysis reactor, obtained during the course of the trial described in Example 14, is delivered onto 0.5 liters of a foraminous Raney nickel catalyst in beads of 2 to 5.5 mm, arranged in a tubular reactor, through whose double jacket steam passes and which has an internal diameter of 25 mm. This catalyst has been obtained by soda action (by means of an aqueous solution of sodium hydroxide containing 50 g/l), at 100° C., on 40% by weight of the aluminum contained in the initial Raney alloy (50% nickel—50% aluminum).

The slightly colored liquid effluent is reheated to about 120° C. and treated on this catalyst at a flow rate of 10.7 l/h, at 116° C., under an absolute pressure of 8 bars, in the presence of hydrogen whose purge flow rate is about 50 Nl/h. After 6 hours of continuous operation under these operating conditions, no appearance of acetaldehyde manifested itself, and the post-catalytic effluent obtained is perfectly colorless, making it possible to obtain a satisfactory commercial product by distillation.

It is likewise possible to operate in the following manner: use is made of 0.5 liters of a catalyst based on nickel (45%) deposited on silica, in the form of pellets having dimensions of 5×5 mm, and having been prereduced in a mixture of water/isobutanol.

The liquid effluent from the catalysis reactor described in Example 14, which contains 0.02 mole of acetaldehyde per kg, is delivered onto the above catalyst at a flow rate of 12 liters/h, and no trace of aldehyde is detected any longer at the outlet of the post-catalysis reactor, with the effluent having thus been obtained likewise having become perfectly colorless.

This effluent can then be subjected to a distillation, without any disadvantage.

EXAMPLE 16

This example illustrates the possibility of a continuous operation of long duration of a catalysis reactor charged with the catalyst described in Example 1 and coupled to a post-catalysis reactor such as described in Example 15. This catalytic set-up furnishes a reaction effluent having been rid of acetaldehyde and being perfectly colorless.

The catalysis reactor contains 2 liters (~2,800 g) of the catalyst described in Example 1 (copper chromite).

The post-catalysis reactor, which receives the liquid reaction effluent from the first reactor, is charged with 0.75 liter of a catalyst based on nickel (45%) deposited on silica, in extrudates having a length of 5 mm and a diameter of 3 mm, and having been prereduced in a water/isobutanol mixture.

The operating conditions of the first catalyst (in pellets of 4.5×4.5 mm), reduced as in Example 1, are the following:

during 750 hours:
(a) salts bath temperature=200° C.,
(b) absolute pressure=8 bars,
(c) flow rate of pure ethanol=2,073 g/h (45.0 moles/h),
(d) flow rate of dimethylamine=649 g/h (14.4 moles/h), and
(e) flow rate of hydrogen=5,342 Nl/h (239 moles/h).
That is to say, with the following molar ratios:

(dimethylamine/ethanol)=0.32

(hydrogen/ethanol)=5.3

The bath temperature was then raised by 2° C. until the 785th hour of operation, and then again by 3° C., i.e., to 205° C., until the 942nd hour of operation. At the 850th hour of operation, the molar ratio of (hydrogen/ethanol) was reduced to 4.

At the 942nd hour of operation, the temperature of the bath was lowered again to 200° C.

The post-catalyst consisting of nickel deposited on silica functioned during 845 hours under the following conditions:
(a) temperature=112° C.,
(b) absolute pressure=7 bars, and
(c) flow rate of condensed liquid to be treated (containing 0.02 mole of acetaldehyde per kg)=3.6 liters/h.

The mean results which follow were obtained:
(i) degree of conversion of the theoretically convertible ethanol: 100.5%,
(ii) degree of conversion of the dimethylamine: 99.9%,
(iii) yield of dimethylethylamine in relation to the converted ethanol: 97.4%, and
(iv) weight percentages of the principal by-products in relation to the dimethylethylamine formed in the crude reaction effluent (at the outlet of the post-catalysis reactor):

| | |
|---|---|
| 1. trimethylamine | 0.97% |
| 2. methyldiethylamine | 0.89% |
| 3. triethylamine | 0.13% |
| 4. dimethylbutylamine | 0.18% |
| 5. methanol | 0.10% |
| 6. residual dimethylamine | 0.07% (as against 0.5 to 1% at the outlet of the catalysis reactor) |

7. acetaldehyde at the outlet of the catalysis reactor 0.011 to 0.036 mole/kg
8. acetaldehyde at the outlet of the post-catalysis reactor: nil (silver mirror test is negative)

No drop in activity was registered in 845 hours of functioning of the post-catalyst. Furthermore, it was possible to effectively compensate for the slight loss in activity of the first catalyst in 950 hours of operation by a drop in the molar ratio of (hydrogen/ethanol).

EXAMPLE 17

This example illustrates the possibility of regenerating the main catalyst by oxidation of the carbonaceous matter by a mixture composed of air diluted with nitrogen and subsequent reduction by a mixture of hydrogen and steam (water vapor) as in Example 1 and in the same equipment set-up.

The operating mode chosen for this oxidation is the following:
(a) salts bath temperature=200° C.,
(b) peak temperature measured in the well of the reactor=300° C.,
(c) molar ratio of (nitrogen/air) regulated in such a way so as not to exceed the temperature of 300° C., and
(d) water flow rate (oxidation initiator)=80 g during 45 minutes.

The peak temperature then moves steadily toward the top of the catalyst, for a duration of 5 hours.

The catalyst is then put under a current of pure air at 450° C. and then the reduction is conducted at 230° C. as in Example 1.

A test of the activity of the regenerated catalyst was carried out under the operating conditions of Example 16, for 4 hours.

A very slight drop in activity was recorded as compared to the catalyst when new and not having been treated by oxidation (weight percentage of unconverted dimethylamine in relation to the dimethylethylamine obtained = 0.2%).

EXAMPLE 18

This example illustrates the effect of the nature of the catalyst on the results. The trial was carried out in a reactor identical to the one of Example 1, in the presence of 2 liters of a catalyst containing a low percentage of potassium oxide, whose composition by weight, after reduction, is the following:

| | |
|---|---|
| copper | 44.2% |
| chromium | 1.5% |
| potassium | 1.1% |
| silica | 53.2% | that is to say with an atomic ratio of (Cu/Cr) = 23 and an atomic ratio of (K/Cu) = 0.041.

The operating conditions are very close to those of Example 13:
(a) temperature of the bath = 204° C.,
(b) absolute pressure = 8 bars,
(c) flow rate of dimethylamine = 668 g/h (14.81 moles/h),
(d) flow rate of pure ethanol = 2,007 g/h (43.57 moles/h), and
(e) flow rate of hydrogen = 4,883 Nl/h (218 moles/h).

That is to say, with the following molar ratios:

(dimethylamine/ethanol) = 0.34

(hydrogen/ethanol) = 5

The following are the principal results obtained:
(i) degree of conversion of the dimethylamine = 100%, and
(ii) yield of dimethylethylamine in relation to the dimethylamine involved = 91.2%.

The weight percentages of the by-products relative to the dimethylethylamine produced (manufactured) are the following:

| | |
|---|---|
| trimethylamine | 3.8% |
| methyldiethylamine | 5.2% |
| methanol | 0.1% |

EXAMPLE 19

This example illustrates the effect of the nature of the catalyst on the results. The test has been carried out in a reactor identical to the one of Example 1 in the presence of 2 liters of a catalyst prepared in the following manner:

To a suspension composed of 1,751 g of basic copper carbonate Cu Co$_3$, Cu (OH)$_2$ in two liters of water, during a time of about one half hour and under agitation we progressively add a solution of chromic anhydride (1,659 g dissolved in 3 liters of water) and an aqueous solution of ammonia at a concentration of 28% by weight (1,587 ml) while adjusting the precipitation pH to about 7, we subsequently add 512.3 g of barium nitrate Ba (NO$_3$)$_2$.

A precipitate of complex basic copper and barium chromates is formed.

To this precipitate, we add 14.5 g of magnesia MgO and 185.5 g of zinc oxide ZnO.

This suspension is evaporated so as to obtain a homogeneous paste which is dried at 140° C. The temperature is then raised to 270° C. for a quarter of an hour.

2.5 to 3 kg of powder are obtained with which a paste is formed by the addition of about 2 liters of water by malaxating (mixing, kneading) for a half an hour. We then add 3% of LUVISKOL K 90 (registered trademark of BASF) and malaxating is again undertaken for a quarter of an hour. Drying is then undertaken at 130°–140° C. in the oven.

After crushing and sifting, pelletization is undertaken after the addition of 2% of graphite. The compressed briquettes obtained are calcined (baked) for 2 hours at 300° C. and ready to be used.

The composition by weight prior to reduction is the following:

copper oxide = 41.65%
chromium sesquioxide = 41.65%
barium oxide = 10.00%
magnesium oxide = 0.50%
zinc oxide = 6.20%

We thus have the following atomic ratios:

(Cu/Cr) = 0.95

(Ba/Cu) = 0.116

(Mg/Cu) = 0.023

(Zn/Cu) = 0.144

The operating conditions are the following ones:
(a) bath temperature = 200° C.,
(b) absolute pressure = 8 bars,
(c) flow rate of the dimethylamine = 642 g/h (14.25 moles/h)
(d) flow rate of the ethanol (at 6.4% water content) calculated as pure ethanol = 2,075 g/h (45.04 moles/h),
(e) flow rate of the hydrogen = 5,040 Nl/h (225 moles/h).

The operation thus takes place with the following molar ratios:

(dimethylamine/ethanol) = 0.32

(hydrogen/ethanol) = 5

Here are the results obtained:
(i) degree of conversion of the dimethylamine = 100%,
(ii) yield of dimethylethylamine in relation to the dimethylamine involved = 97.5%.

The percentages of the by-products by weight, in relation to the dimethylethylamine produced (manufactured) are the following:

| | |
|---|---|
| trimethylamine | 1.2% |
| methyldiethylamine | 1.1% |
| triethylamine | 0.1% |
| methanol | 0.1% |

EXAMPLE 20

The test was carried out in a reactor identical to the one used in Example 1 in the presence of 2 liters of a catalyst prepared in the following manner:

The following two solutions are prepared:
A. Cupric solution
water=2,610 ml
ammonium hydroxide at 30% by weight=6,268 ml
basic copper carbonate=2,610 g Cu $CO_3$, $Cu(OH)_2$
B. Chromic solution
chromic anhydride (Cr $O_3$)=474 g
magnesium oxide (MgO)=90 g
water=474 g The following is placed in a malaxator (mixer):
solution A to which one quarter of solution B has been added.

Little by little (gradually) 1,050 g of zinc oxide ZnO are added. When the mixture is homogeneous, the remainder of solution B is added.

The paste having been obtained is dried at 140° C. for 12 hours and then the temperature is raised to 270° C. for one half an hour and to 330° C. for two hours.

After crushing, the powder thus having been obtained is made into the form of a paste (dough) with 3% of LUVISKOL K90 (registered trademark of BASF) and a sufficient quantity of water in order to obtain dry granules. After malaxation (mixing, kneading), drying and sifting, the granules are made into pellets with 2% of graphite.

The composition by weight of this catalytic formula after reduction is the following:

| | |
|---|---|
| copper | 50% |
| magnesium oxide | 3% |
| chromium sesquioxide | 12% |
| zinc oxide | 35% | which corresponds to the following atomic ratios:

(Cu/Cr)=5

(Mg/Cu)=0.094

(Zn/Cu)=0.546

The operating conditions are very close to those of Example 1:
(a) bath temperature=200° C.,
(b) absolute pressure=8 bars,
(c) flow rate of the dimethylamine=635 g/h (14.09 moles/h),
(d) flow rate of the hydrogen=5,040 Nl/h (225 moles/h), that is to say the molar ratios are the following:

(dimethylamine/ethanol)=0.31

(hydrogen/ethanol)=5

Here are the results obtained:
(i) degree of conversion of the dimethylamine=93.6%,
(ii) yield of dimethylethylamine in relation to the dimethylamine converted=97.6%.

The weight percentages of the by-products in relation to the dimethylethylamine produced (manufactured) are the following:

| | |
|---|---|
| trimethylamine | 0.9% |
| methyldiethylamine | 1.0% |
| methylethylamine | 0.2% |
| triethylamine | 0.2% |
| methanol | 0.2% |

EXAMPLE 21

This example illustrates the possibility of reducing the excess of ethanol in relation to the dimethylamine involved. The test was carried out in a reactor identical to the one of Example 1, in the presence of 2 liters of the catalyst described in Example 20.

The operating conditions are the following ones:
(a) bath temperature=200° C.,
(b) absolute pressure=8 bars,
(c) flow rate of the dimethylamine=344 g/h (7.64 moles/h),
(d) flow rate of the pure ethanol=693 g/h (15.03 moles/h), and
(e) flow rate of the hydrogen=3,651 Nl/h (163 moles/h).

That is to say the molar ratios are the following:

(dimethylamine/ethanol)=0.51

(hydrogen/ethanol)=10.8

Here are the results obtained:
(i) degree of conversion of the dimethylamine=100%,
(ii) yield of dimethylethylamine in relation to the dimethylamine involved=97.1%,
(iii) degree of conversion of the theoretically convertible ethanol=103.9%, and
(iv) yield of dimethylethylamine in relation to the converted ethanol=97.0%.

The percentages of the by-products by weight, in relation to the dimethylethylamine produced (manufactured) are the following:

| | |
|---|---|
| trimethylamine | 1.5% |
| methyldiethylamine | 1.3% |
| triethylamine | 0.1% |
| methanol | 0.1% |

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A process for the manufacture of dimethylethylamine comprising reacting gaseous ethanol with a gaseous mixture of hydrogen and dimethylamine in the presence of a hydrogenation/dehydrogenation catalyst comprising copper and chromic oxide alone or admixed with barium oxide, zinc oxide, magnesium oxide, or other oxides, at a temperature of about 180° to 240° C. and an absolute pressure of about 1 to 15 bars for a time sufficient to form dimethylethylamine, the molar ratio of dimethylamine/ethanol being about 0.2 to 0.6 and the molar ratio of hydrogen/ethanol being about 3 to 10.

2. The process of claim 1 wherein the temperature is about 200° to 210° C., the molar ratio of dimethylamine/ethanol is about 0.25 to 0.4, and the molar ratio of hydrogen/ethanol is about 4 to 7.

3. The process of claim 1 or 2 wherein the process is carried out continuously and the unreacted gases are recycled for further reaction with 0.1 to 1% by volume of the recycled gases being replaced by hydrogen.

4. The process of claim 1 or 2 in which the flow rate of ethanol is from about 10 to 50 moles/hour per liter of catalyst.

5. The process of claim 1 in which the effluent from the reaction is treated on a hydrogenation catalyst at a temperature of about 100° to 130° C. and at a pressure essentially the same as that used in said reaction.

6. The process of claim 5, in which the hydrogenation catalyst for the effluent is identical to the catalyst used in said reaction.

7. The process according to claim 5, in which the hydrogenation catalyst for the liquid effluent is foraminous Raney nickel of 2 to 10 mm size.

8. The process of claim 5, in which the hydrogenation catalyst for the liquid effluent consists of nickel deposited on a silica support, used in the form of pellets of 3 to 10 mm size.

9. The process of claims 1 or 2 in which the effluent is treated in continuous manner with hydrazine hydrate.

10. The process of claims 1, 2 or 5 in which the reaction is conducted in the presence of a catalytic mass having undergone a regeneration consisting of an oxidation by a mixture of air diluted in nitrogen, followed by a reduction by a mixture of hydrogen and steam.

11. A process for the manufacture of dimethylethylamine comprising reacting, on a continuous basis, gaseous ethanol with a gaseous mixture of hydrogen and dimethylamine in the presence of a hydrogenation/dehydrogenation catalyst comprising copper and chromic oxide alone or admixed with barium oxide, zinc oxide, magnesium oxide, or other oxides, at a temperature of about 200° to 210° C. and an absolute pressure of about 1 to 15 bars for a time sufficient to form a reaction effluent containing dimethylethylamine, separating the unreacted gases from the reaction effluent, treating said reaction effluent with a hydrogenation catalyst at a temperature of 100° to 130° C. and at a pressure essentially the same as that used in forming the reaction effluent, recycling the separated gases for further reaction with about 0.2 to 0.7% by volume of the recycled gases being replaced by hydrogen, and recovering dimethylethylamine, the molar ratio of dimethylamine/ethanol being about 0.25 to 0.4, the molar ratio of hydrogen/ethanol being about 3 to 10, and the flow rate of the ethanol is from about 20 to 25 moles/hour per liter of catalyst.

* * * * *